United States Patent [19]

Rosentreter et al.

[11] Patent Number: 4,853,406

[45] Date of Patent: Aug. 1, 1989

[54] POLYHYDROBENZI[C,D]INDOLESULPHONAMIDES

[75] Inventors: Ulrich Rosentreter, Wuppertal; Horst Böshagen, Haan; Folker Lieb, Leverkusen; Hermann Oediger, Cologne; Ulrich Niewöhner, Wermelskirchen; Friedel Seuter; Elisabeth Perzborn, both of Wuppertal; Volker-Bernd Fiedler, Leverkusen, all of Fed. Rep. of Germany

[73] Assignee: Bayer Aktiengesellschaft, Leverkusen, Fed. Rep. of Germany

[21] Appl. No.: 200,342

[22] Filed: May 31, 1988

[30] Foreign Application Priority Data

Jun. 5, 1987 [DE] Fed. Rep. of Germany ....... 3718892

[51] Int. Cl.$^4$ ..................... A61K 31/40; C07D 209/92
[52] U.S. Cl. .................................. 514/411; 548/436; 548/438
[58] Field of Search ................. 548/436, 438; 514/411

[56] References Cited

U.S. PATENT DOCUMENTS 4,501,900 2/1985 Baldwin et al. ..................... 548/436
4,576,959 3/1986 Flaugh ................................ 548/436

Primary Examiner—Mary E. Ceperley
Attorney, Agent, or Firm—Sprung Horn Kramer & Woods

[57] ABSTRACT

Thrombocyte aggregation-inhibiting polyhydrobenz[c,d]indolesulphonamide of the formula

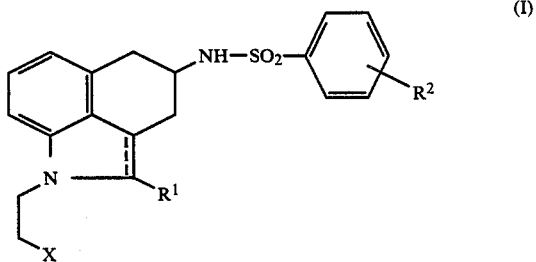

(I)

in which
R$^1$ is hydrogen, aryl or alkyl,
R$^2$ is hydrogen, halogen, alkyl, alkoxy, trifluoromethyl, trifluoromethoxy, hydroxyl, aralkoxy or a group of the formula

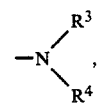

R$^3$ and R$^4$ each independently is hydrogen, alkyl, aryl, aralkyl or acyl and
X is cyano or carboxyl, and salts thereof. Intermediates therefor of the formula

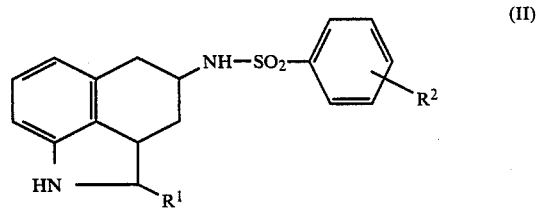

(II)

are also new.

14 Claims, No Drawings

POLYHYDROBENZI[C,D]INDOLESULPHONAMIDES

The invention relates to new polyhydrobenz[c,d]indolesulphonamides, a process for their preparation and their use in medicaments.

New polyhydrobenz[c,d]indolesulphonamides of the general formula (I)

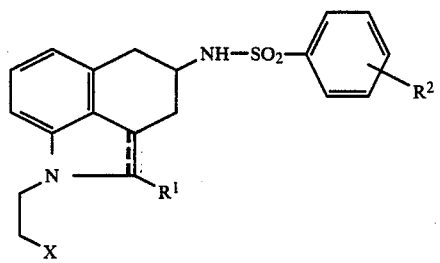

in which
$R^1$ represents hydrogen, aryl or alkyl,
$R^2$ represents hydrogen, halogen, alkyl, alkoxy, trifluoromethyl, trifluoromethoxy, hydroxyl, aralkoxy or
a group of the formula

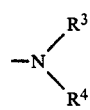

wherein
$R^3$ and $R^4$ are identical or different and denote hydrogen, alkyl, aryl, aralkyl or acyl and
X represents cyano or carboxyl, and their salts, have been found.

The substances according to the invention surprisingly show a thrombocyte aggregation-inhibiting action and can be used for therapeutic treatment of humans and animals.

The polyhydrobenz[c,d]indolesulphonamides according to the invention can also exist in the form of their salts. In general, salts with inorganic or organic bases may be mentioned here.

Physiologically acceptable salts are preferred within the scope of the present invention. Physiologically acceptable salts of the polyhydrobenz[c,d]indolesulphonamides can be metal salts or ammonium salts of the substances according to the invention which carry a free carboxyl group (X=COOH). For example, salts of sodium, potassium, magnesium or calcium, and also ammonium salts which are derived from ammonia or organic amides, such as, for example, ethylamine, diethylamine, triethylamine, diethanolamine, triethanolamine, dicyclohexylamine, dimethylaminoethanol, arginine or ethylenediamine, are particularly preferred.

The polyhydrobenz[c,d]indolesulphonamides according to the invention have several asymmetric carbon atoms and can therefore exist in various stereoisomeric forms. The invention relates both to the individual isomers and to their mixtures. For example, the following isomeric forms of the polyhydrobenz[c,d]indolesulphonamides may be mentioned:

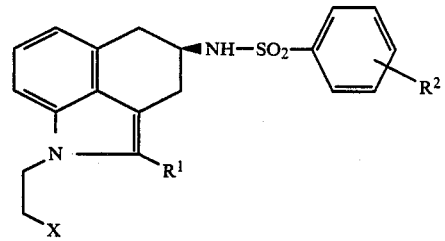

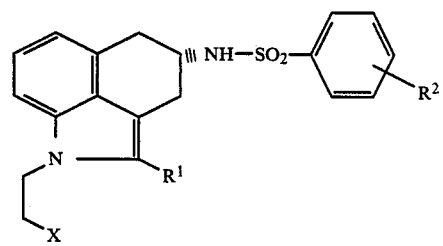

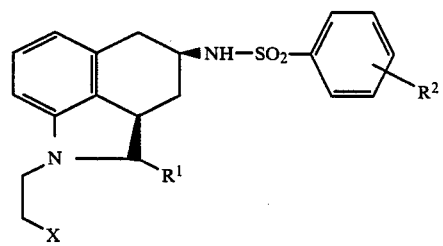

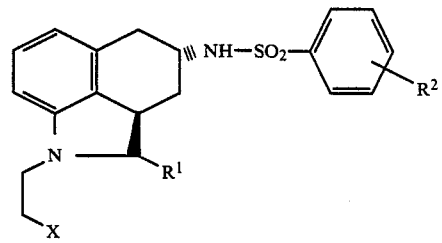

in which
$R^1$, $R^2$ and X have the abovementioned meaning.

*Alkyl* generally represents a branched hydrocarbon radical having 1 to 12 carbon atoms. Lower alkyl having 1 to about 6 carbon atoms is preferred. For example, methyl, ethyl, propyl, isopropyl, butyl, isobutyl, pentyl, isopentyl, hexyl, isohexyl, heptyl, isoheptyl, octyl and isooctyl may be mentioned.

*Aryl* generally represents an aromatic radical having 6 to about 12 carbon atoms. Phenyl, naphthyl and biphenyl are preferred aryl radicals.

*Aralkyl* generally represents an aryl radical having 7 to 14 carbon atoms which is bonded through an alkylene chain. Aralkyl radicals having 1 to 6 carbon atoms in the aliphatic part and 6 to 12 carbon atoms in the aromatic part are preferred. For example, the following aralkyl radicals may be mentioned: benzyl, naphthylmethyl, phenethyl and phenylpropyl.

*Alkoxy* generally represents a straight-chain or branched hydrocarbon radical having 1 to 12 carbon atoms which is bonded through an oxygen atom. Lower alkoxy having 1 to about 6 carbon atoms is preferred. An alkoxy radical having 1 to 4 carbon atoms is particularly preferred. For example, methoxy, ethoxy, propoxy, isopropoxy, butoxy, isobutoxy, pentoxy, isopentoxy, hexoxy, isohexoxy, heptoxy, isoheptoxy, octoxy or isooctoxy may be mentioned.

*Aralkoxy* generally represents an aralkyl radical having 7 to 14 carbon atoms in which the alkylene chain is bonded through an oxygen atom. Aralkoxy radicals haviing 1 to 6 carbon atoms in the aliphatic part and 6 to 12 carbon atoms in the aromatic part are preferred. For example, the following aralkoxy radicals may be mentioned: benzyloxy, naphthylmethoxy, phenethoxy and phenylpropoxy.

*Acyl* generally represents phenyl or straight-chain or branched lower alkyl having 1 to about 6 carbon atoms, which are bonded through a carbonyl group. Phenyl and alkyl radicals having up to 4 carbon atoms are preferred. For example: benzoyl, acetyl, ethylcarbonyl, propylcarbonyl, isopropylcarbonyl, butylcarbonyl and isobutylcarbonyl may be mentioned.

*Halogen* generally represents fluorine, chlorine, bromine or iodine, preferably fluorine, chlorine or bromine. Halogen particularly preferably represents fluorine or chlorine.

Preferred compounds of the general formula (I) are those in which $R^1$ represents hydrogen, phenyl or lower alkyl, $R^2$ represents hydrogen, fluorine, chlorine, bromine, lower alkyl, lower alkoxy, trifluoromethyl, hydroxyl, benzyloxy or a group of the formula

wherein $R^3$ and $R^4$ are identical or different and denote hydrogen, lower alkyl, phenyl, benzyl or acetyl and X represents cyano or carboxyl, and their salts.

Particularly preferred compounds of the general formula (I) are those in which $R^1$ represents hydrogen, methyl, ethyl, propyl or isopropyl, $R^2$ represents hydrogen, fluorine, chlorine, methyl, ethyl, propyl, isopropyl, methoxy, ethoxy, propoxy, isopropoxy, trifluoromethyl or a group of the formula

wherein $R^3$ and $R^4$ are identical or different and denote hydrogen, methyl, ethyl or propyl and X represents cyano or carboxyl, and their salts.

For example, the following polyhydrobenz[c,d]indolesulphonamides may be mentioned:

1-(2-cyanoethyl)-4-(4-fluorophenyl-sulphonamido)-1,2,2a,3,4,5-hexahydrobenz[c,d]indole;
1-(2-carboxyethyl)-4-(4-fluorophenyl-sulphonamido)-1,2,2a,3,4,5-hexahydrobenz[c,d]indole;
1-(2-cyanoethyl)-4-(4-fluorophenyl-sulphonamido)-1,3,4,5-tetrahydrobenz[c,d]indole;
1-(2-carboxyethyl)-4-(4-fluorophenyl-sulphonamido)-1,3,4,5-tetrahydrobenz[c,d]indole;
1-(2-cyanoethyl)-4-(4-chlorophenyl-sulphonamido)-1,2,2a,3,4,5-hexahydrobenz[c,d]indole;
1-(2-carboxyethyl)-4-(4-chlorophenyl-sulphonamido)-1,2,2a,3,4,5-hexahydrobenz[c,d]indole;
1-(2-cyanoethyl)-4-(4-chlorophenyl-sulphonamido)-1,3,4,5-tetrahydrobenz[c,d]indole;
1-(2-carboxyethyl)-4-(4-chlorophenyl-sulphonamido)-1,3,4,5-tetrahydrobenz[c,d]indole;
1-(2-cyanoethyl)-4-(4-methylphenyl-sulphonamido)-1,2,2a,3,4,5-hexahydrobenz[c,d]indole;
1-(2-carboxyethyl)-4-(4-methylphenyl-sulphonamido)-1,2,2a,3,4,5-hexahydrobenz[c,d]indole;
1-(2-cyanoethyl)-4-(4-methylphenyl-sulphonamido)-1,3,4,5-tetrahydrobenz[c,d]indole;
1-(2-carboxyethyl)-4-(4-methylphenyl-sulphonamido)-1,3,4,5-tetrahydrobenz[c,d]indole;
1-(2-cyanoethyl)-4-(4-methoxyphenyl-sulphonamido)-1,2,2a,3,4,5-hexahydrobenz[c,d]indole;
1-(2-carboxyethyl)-4-(4-methoxyphenyl-sulphonamido)-1,2,2a,3,4,5-hexahydrobenz[c,d]indole;
1-(2-cyanoethyl)-4-(4-methoxyphenyl-sulphonamido)-1,3,4,5-tetrahydrobenz[c,d]indole;
1-(2-carboxyethyl)-4-(4-methoxyphenyl-sulphonamido)-1,3,4,5-tetrahydrobenz[c,d]indole;
1-(2-cyanoethyl)-4-(3-fluorophenyl-sulphonamido)-1,2,2a,3,4,5-hexahydrobenz[c,d]indole;
1-(2-carboxyethyl)-4-(3-fluorophenyl-sulphonamido)-1,2,2a,3,4,5-hexahydrobenz[c,d]indole;
1-(2-cyanoethyl)-4-(3-fluorophenyl-sulphonamido)-1,3,4,5-tetrahydrobenz[c,d]indole;
1-(2-carboxyethyl)-4-(3-fluorophenyl-sulphonamido)-1,3,4,5-tetrahydrobenz[c,d]indole;
1-(2-cyanoethyl)-4-(3-chlorophenyl-sulphonamido)-1,2,2a,3,4,5-hexahydrobenz[c,d]indole;
1-(2-carboxyethyl)-4-(3-chlorophenyl-sulphonamido)-1,2,2a,3,4,5-hexahydrobenz[c,d]indole;
1-(2-cyanoethyl)-4-(3-chlorophenyl-sulphonamido)-1,3,4,5-tetrahydrobenz[c,d]indole;
1-(2-carboxyethyl)-4-(3-chlorophenyl-sulphonamido)-1,3,4,5-tetrahydrobenz[c,d]indole;
1-(2-cyanoethyl)-4-(3-methylphenyl-sulphonamido)-1,2,2a,3,4,5-hexahydrobenz[c,d]indole;
1-(2-carboxyethyl)-4-(3-methylphenyl-sulphonamido)-1,2,2a,3,4,5-hexahydrobenz[c,d]indole;
1-(2-cyanoethyl)-4-(3-methylphenyl-sulphonamido)-1,3,4,5-tetrahydrobenz[c,d]indole;
1-(2-carboxyethyl)-4-(3-methylphenyl-sulphonamido)-1,3,4,5-tetrahydrobenz[c,d]indole;
1-(2-cyanoethyl)-4-(3-methoxyphenyl-sulphonamido)-1,2,2a,3,4,5-hexahydrobenz[c,d]indole;
1-(2-carboxyethyl)-4-(3-methoxyphenyl-sulphonamido)-1,2,2a,3,4,5-hexahydrobenz[c,d]indole;
1-(2-cyanoethyl)-4-(3-methoxyphenyl-sulphonamido)-1,3,4,5-tetrahydrobenz[c,d]indole;
1-(2-carboxyethyl)-4-(3-methoxyphenyl-sulphonamido)-1,3,4,5-tetrahydrobenz[c,d]indole;

Furthermore, a process has been found for the preparation of the polyhydrobenz[c,d]indolesulphonamides of the general formula (I) according to the invention

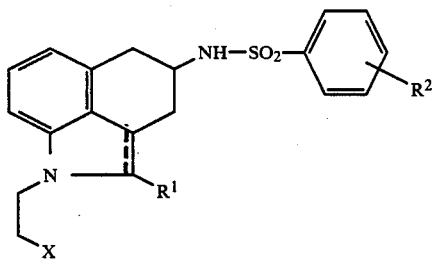

(I)

in which
R[1] represents hydrogen, aryl or alkyl,
R[2] represents hydrogen, halogen, alkyl, alkoxy, trifluoromethyl, trifluoromethoxy, hydroxyl, aralkoxy or
a group of the formula

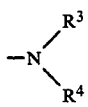

wherein
R[3] and R[4] are identical or different and denote hydrogen, alkyl, aryl, aralkyl or acyl and
X represents cyano or carboxyl, and their salts, which is characterized in that N-substituted hexahydrobenzoindolesulphonamides of the general formula (II)

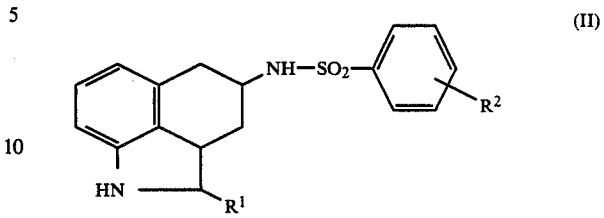

(II)

in which
R[1] and R[2] have the abovementioned meaning, are reacted with acrylonitrile in the presence of an inert solvent and if appropriate in the presence of a catalyst,
in the case of the preparation of the tetrahydrobenzoindole sulphonamides, the hexahydrobenzoindolesulphonamides are then reacted with an oxidant in the presence of an inert solvent,
in the case of the preparation of the carboxyl compounds (X=COOH), the cyano compounds (X=CN) are then hydrolyzed,
and, in the case of the preparation of the salts the products are reacted with the appropriate bases.

The process according to the invention can be illustrated by the following equation:

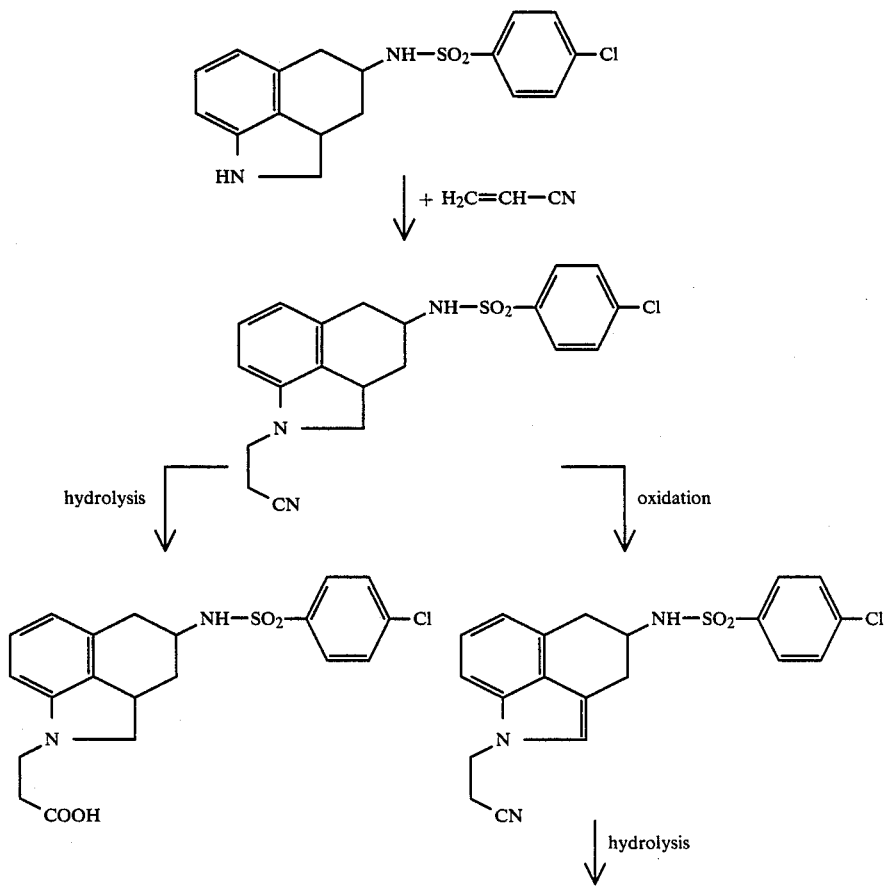

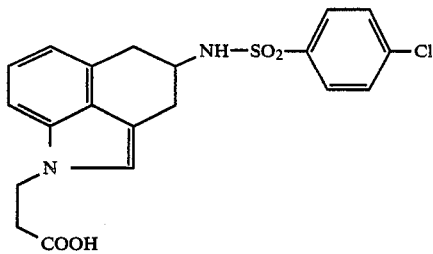

The tetrahydrobenzoindolesulphonamides encompassed by the formula (I) correspond to the formula (Ia)

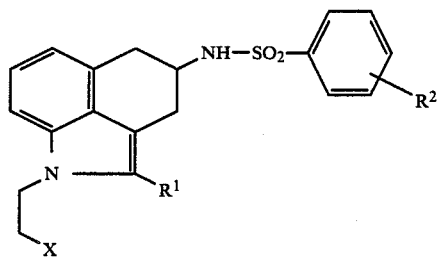
(Ia)

in which
$R^1$, $R^2$ and X have the abovementioned meaning.

The hexahydrobenzoindolesulphonamides encompassed by the formula (I) correspond to the formula (Ib)

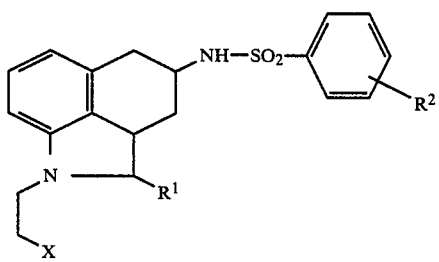
(Ib)

in which
$R^1$, $R^2$ and X have the abovementioned meaning.

In carrying out the process according to the invention, intermediates which can be isolated generally result. It is thus possible to carry out the process according to the invention in several process steps. It may also be possible, however, to combine different steps of the process.

Suitable solvents for the reaction with acrylonitrile are the customary organic solvents which do not react under the reaction conditions. These preferably include alcohols such as methanol, ethanol, propanol, isopropanol or butanol, or hydrocarbons such as benzene, toluene, xylene, hexane, cyclohexane or mineral oil fractions. Likewise, it is possible to use mixtures of the solvents mentioned. In some cases it has also proved favorable to employ acrylonitrile directly as the solvent in a large excess.

Suitable catalysts for the reaction with acrylonitrile are, where appropriate, copper salts, mercury salts, palladium salts or organic palladium compounds. These preferably include copper halides such as, for example, copper chloride, or copper sulphate, copper acetate or copper acetonyl acetonate, or mercury halides such as, for example, mercury chloride.

The reaction with acrylonitrile is generally carried out in a temperature range from 0° C. to +200° C., preferably from +50° C. to +150° C.

The reaction with acrylonitrile according to the invention is generally carried out at atmospheric pressure. However, it is also possible to carry out the reaction at elevated pressure, for example preferably in a range from 5,000 to 20,000 bar, preferably in a range from 7,000 to 15,000 bar.

In general, 1 to 20 moles, preferably 1 to 10 moles, of acrylonitrile are employed per mole of N-unsubstituted hexahydrobenzindolesulphonamide. The reaction is particularly preferably carried out using acrylonitrile as the solvent in an excess of up to 100 fold, preferably up to 50 fold.

In the reaction of the tetrahydrobenzoindolesulphonamides with oxidants, suitable solvents are the customary organic solvents which under the reaction conditions do not react. These preferably include hydrocarbons such as benzene, toluene, xylene, hexane, cyclohexane or mineral oil fractions, or halogenated hydrocarbons such as methylene chloride, chloroform, carbon tetrachloride, dichloroethane or chlorobenzene. Likewise, it is possible to use mixtures of the solvents mentioned.

Suitable oxidants are the customary inorganic or organic oxidants which are customarily used for the conversion of a hydro-compound into a dehydro-compound. These preferably include inorganic compounds such as bromine, chlorine or manganese dioxide, or organic halogen compounds such as, for example, N-chlorosuccinimide, N-bromosuccinimide, chloranil or dichlorodicyanobenzoquinone. Chloranil is particularly preferably used.

The oxidation is generally carried out in a temperature range from +20° C. to +200° C., preferably from +50° C. to +150° C.

The oxidation is generally carried out at atmospheric pressure. However, it is also possible to carry out the oxidation at reduced pressure or at elevated pressure (for example in a range from 0.5 to 5 bar).

In general, 1 to 5, preferably 2 to 3, moles of oxidant are employed per mole of hexahydrobenzoindolesulphonamide.

The hydrolysis of the cyano compound takes place in a manner which is known per se in the presence of bases, such as hydroxides or alcoholates of alkali metals or alkaline earth metals, in inert solvents such as water or alcohol. Bases which are preferably used are sodium hydroxide, potassium hydroxide or barium hydroxide, sodium methanolate, potassium methanolate, sodium ethanolate or potassium ethanolates or potassium tert.

butanolate, preferably in water or methanol, ethanol, propanol or isopropanol, or in mixtures of these solvents.

In general, 1 to 100 moles, preferably 2 to 50 moles, of base are employed per mole of cyano compound.

The hydrolysis is generally carried out in a temperature range from 0° C. to +100° C., preferably from +20° C. to +80° C.

The following N-unsubstituted hexahydrobenzindolesulphonamides of the formula (II) are employed, for example, according to the invention:

4-(4-fluorophenyl-sulphonamido)-1,2,2a,3,4,5-hexahydrobenz[c,d]indole;
4-(4-chlorophenyl-sulphonamido)-1,2,2a,3,4,5-hexahydrobenz[c,d]indole;
4-(4-methylphenyl-sulphonamido)-1,2,2a,3,4,5-hexahydrobenz[c,d]indole;
4-(4-methoxyphenyl-sulphonamido)-1,2,2,a,3,4,5-hexahydrobenz[c,d]indole;
4-(3-fluorophenyl-sulphonamido)-1,2,2a,3,4,5-hexahydrobenz[c,d]indole;
4-(3-chlorophenyl-sulphonamido)-1,2,2a,3,4,5-hexahydrobenz[c,d]indole;
4-(3-methylphenyl-sulphonamido)-1,2,2a,3,4,5-hexahydrobenz[c,d]indole;
4-(3-methoxyphenyl-sulphonamido)-1,2,2a,3,4,5-hexahydrobenz[c,d]indole The N-unsubstituted hexahydrobenzoindolesulphonamides of the general formula (II) are new.

In addition, a process has been found or the preparation of the N-unsubstituted hexahydrobenzindolesulphonamides of the general formula (II)

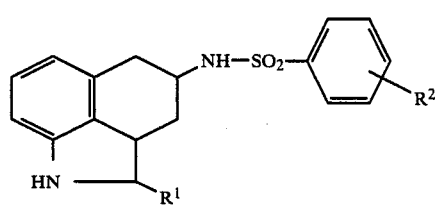

(II)

in which
R$^1$ represents hydrogen, aryl or alkyl, and
R$^2$ represents hydrogen, halogen, alkyl, alkoxy, trifluoromethyl, trifluoromethoxy, hydroxyl, aralkoxy or
a group of the formula

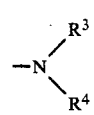

wherein
R$^3$ and R$^4$ are identical or different and denote hydrogen, alkyl, aryl, aralkyl or acyl
which is characterized in that amino compounds of the general formula (III)

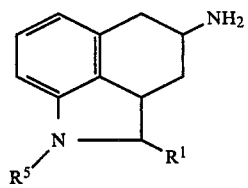

(III)

in which
R$^1$ has the abovementioned meaning and
R$^5$ represents acyl, preferably benzoyl, are reacted with sulphonyl halides of the general formula (IV)

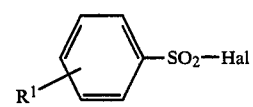

(IV)

in which
R$^1$ has the abovementioned meaning and
Hal represents fluorine, chlorine, bromine, iodine, preferably chlorine or bromine, in inert solvents, if appropriate in the presence of bases and the acyl group is then removed.

The process according to the invention can be illustrated by the following equation, for example:

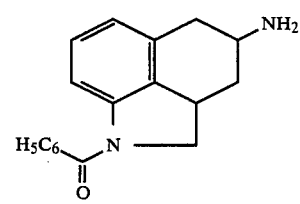

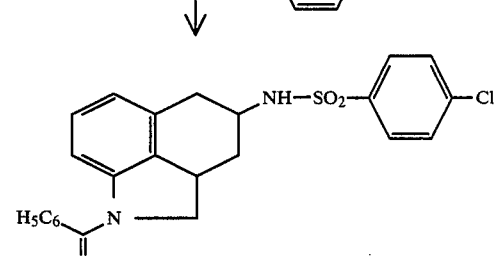

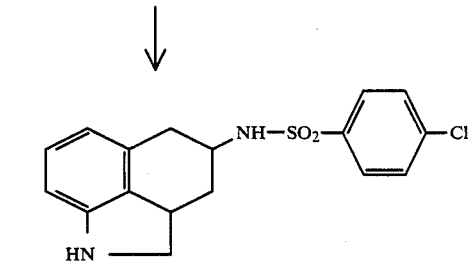

Suitable solvents in this process are the customary organic solvents which are not changed under the reaction conditions. These preferably include ethers such as diethyl ether, dioxane, tetrahydrofuran or glycol dimethyl ether, or hydrocarbons such as benzene, toluene, xylene, hexane, cyclohexane or mineral oil fractions, or halogenated hydrocarbons such as dichloromethane, trichloromethane, tetrachloromethane, dichloroethylene, trichloroethylene or chlorobenzene, or ethyl acetate, triethylamine, pyridine, dimethyl sulphoxide, or amides such as dimethylformamide, dimethylacetamide, hexamethylphosphoric triamide, or acetonitrile, acetone or nitromethane. Likewise, it is possible to employ mixtures of the solvents mentioned.

Bases which can be employed are customary basic compounds. These preferably include hydroxides of alkali metals or alkaline earth metals such as lithium hydroxide, sodium hydroxide, potassium hydroxide or barium hydroxide, or alkali metal hydrides such as sodium hydride, or carbonates of alkali metals or alkaline earth metals such as sodium carbonate, sodium hydrogen carbonate, potassium carbonate or calcium carbonate, or alkali metal alcoholates such as, for example, sodium methanolate, sodium ethanolate, potassium methanolate, potassium ethanolate, or potassium tert-butanolate, or alkali metal amides such as lithium diisopropylamide or sodium amide, or organic amines such as ethyl diisopropylamine, benzyltrimethylammonium hydroxide, tetrabutylammonium hydroxide, pyridine, dimethylaminopyridine, triethylamine, N-methylpiperidine, 1,5-diazabicyclo[4,3,0]non-5-ene or 1,5-diazabicyclo[5,4,0]undec-5-ene.

The process according to the invention is generally carried out in a temperature range from −30° C. to +150° C., preferably from +20° C. to +80° C.

The process according to the invention is generally carried out at atmospheric pressure. However, it is also possible to work at reduced pressure or at elevated pressure (for example in a range from 0.5 to 200 bar).

In general, 1 to 5 moles, preferably 1 to 2 moles, particularly preferably 1 mole, of sulphonyl halide are employed per mole of the amino compound.

The acyl group can be removed by the addition of bases, for example. Suitable bases here are the customary inorganic bases such as hydroxides of alkali metals or alkaline earth metals, for example sodium hydroxide, potassium hydroxide or barium hydroxide, or alkali metal carbonates such as sodium carbonate or potassium carbonate. Suitable solvents here are water or alcohols such as methanol, ethanol, propanol, isopropanol or butanol. Likewise, mixtures of the solvents mentioned can be employed. In general, 1 to 5 moles, preferably 2 to 4 moles, of the base are employed per mole of the acyl compound. The removal of the acyl group is generally carried out in a temperature range from 0° C. to +150° C., preferably from +20° C. to +100° C.

The amino compounds of the general formula (III) employed as starting materials are known or can be prepared by known methods. The preparation can be illustrated by the following equation:

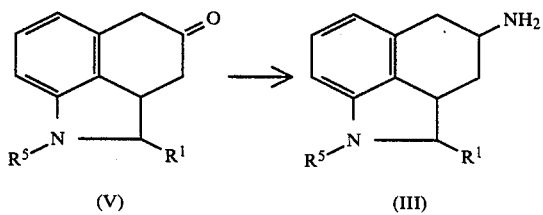

Accordingly, ketones of the general formula (V) are reductively aminated by customary methods using ammonia-containing components in inert solvents, if appropriate in the presence of auxiliaries.

Suitable solvents here are the customary organic solvents which do not react under the reaction conditions. These preferably include alcohols such as methanol, ethanol, propanol or isopropanol, or ethers such as diethyl ether, tetrahydrofuran or dioxane, or chlorinated hydrocarbons such as methylene chloride or chloroform, or acetonitrile, dimethylformamide, dimethyl sulphoxide, glacial acetic acid or mixtures of the solvents mentioned.

Suitable reducing agents are the customary complex hydrides, such as, for example, sodium borohydride, sodium cyanoborohydride, or aminoborane complexes, and also hydrogen, if necessary in the presence of a metal catalyst such as Raney nickel or palladium.

Ammonia-containing components employed are aqueous ammonia solution, gaseous ammonia, or alternatively amonium salts such as ammonium chloride, ammonium sulphate, ammonium acetate or ammonium formate.

The reaction can be carried out at atmospheric, elevated or at reduced pressure (0.5 to 5 bar). In general, the reaction is carried out at atmospheric pressure when using complex metal hydrides or at elevated pressure when using hydrogen.

The reductive amination is generally carried out in a temperature range from 0° C. to +150° C., preferably from +20° C. to +100° C.

The ketones of the general formula (V) employed as starting materials are known or can be prepared by known methods [Kornfeld, Woodward et al., J. Amer. Chem. Soc. 78, 3096 (1956)].

The new polyhydrobenz[c,d]indolesulphonamides or their salts can be employed as active compounds in medicaments. The active compounds exhibit a thrombocyte aggregation-inhibiting action. They can preferably be employed for the treatment of thromboses, thrombo-embolisms, ischaemias, as antiasthmatics and as antiallergics.

The new active compounds can be converted into the customary formulations, such as tablets, dragees, pills, granules, aerosols, syrups, emulsions, suspensions and solutions, in a known manner using inert, non-toxic, pharmaceutically suitable excipients or solvents. In each case the therapeutically active compound should be present here in a concentration of about 0.5 90% by weight of the total mixture, that is in amounts which are sufficient to achieve the abovementioned range in dosage.

The formulations are prepared, for example, by extending the active compounds with solvents and/or carriers, if appropriate using emulsifiers and/or dispersants, in which, for example, in the case of the use of water as diluent, organic solvents can be used as auxiliary solvents if necessary. The following may be mentioned, as example of auxiliaries: water, non-toxic organic solvents, such as paraffins (for example mineral oil fractions), vegetable oils (for example groundnut/sesame oil), alcohols (for example: ethyl alcohol, glycerol), carriers, such as, for example, ground natural minerals (for example kaolins, clays, talc, chalk), ground synthetic minerals (for example highly disperse silica, silicates), sugars (for example sucrose, lactose and dextrose), emulsifiers (for example polyoxyethylene fatty acid esters, polyoxyethylene fatty alcohol ethers, alkylsulphonates and arylsulphonates), dispersants (for example lignin-sulphite waste liquors, methylcellulose, starch and polyvinylpyrrolidone) and lubricants (for example magnesium stearate, talc, stearic acid and sodium laurylsulphate).

Administration takes place in a customary manner, preferably orally or parenterally, in particular perlingually or intravenously. In the case of oral administration, the tablets can of course also contain additives, such as sodium citrate, calcium carbonate and dicalcium phosphate together with various additives such as starch, preferably potato starch, gelatin and the like, in addition to the excipients mentioned. Furthermore, lubricants such as magnesium stearate, sodium laurylsulphate and talc can also be used for tabletting. In the case of aqueous suspensions, various flavor improvers or colorants can be added to the active compounds in addition to the abovementioned auxiliaries.

In general, it has proved advantageous to administer amounts of about 0.001 to 1 mg/kg, preferably about 0.01 to 0.5 mg/kg, of body weight on intravenous administration to obtain effective results, and on oral administration the dosage is about 0.01 to 20 mg/kg, preferably 0.1 to 10 mg/kg, of body weight.

Nevertheless, it may in some cases be necessary to deviate from the amounts mentioned, and in particular to do so as a function of the body weight or the type of administration route, the individual behavior towards the medicament, the nature of its formulation and the point in time or interval at which the administration takes place. Thus, it may be sufficient in some cases to manage with less than the abovementioned minimum amount, whereas in other cases the upper limit mentioned must be exceeded. In the case of administration of larger amounts it may be advisable to divide these into several individual doses over the day.

PREPARATION EXAMPLES

EXAMPLE 1

Intermediate (A)

1-Benzoyl-4-amino-1,2,2a,3,4,5-hexahydrobenz[c,d]indole

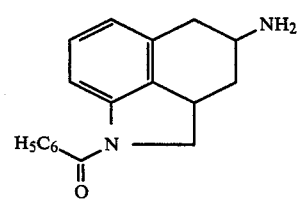

3.5 g of 1-benzoyl-4-oxo-1,2,2a,3,4,5-hexahydro[c,d]indole together with 9.7 g of ammonium acetate are stirred for 2 h in a mixture of 35 ml of dichloromethane and 35 ml of methanol. 0.79 g of sodium cyanoborohydride is then added and the reaction solution is stirred for 1 h at room temperature. For working up, the solution is diluted with 150 ml of ethyl acetate and extracted 4 times with 2N sulphuric acid. The combined aqueous phases are washed using ethyl acetate and rendered alkaline using 20% strength sodium hydroxide solution. The solution is extracted 4 times with dichloromethane, dried using sodium sulphate and evaporated. The residue is chromatographed on 20 g of silica gel 60 using toluene/ethanol as eluant (stepwise alteration of the ratio from 20:1 to 10:1, then to 1:1). A fraction is thus obtained which after evaporation is 2.41 g of a clean product as a solid residue.

Yield: 68.7% of theory
m.p.: 126° C.
$R_f$ value: 0.15 (toluene:ethanol 1:1)

Intermediate (B)

1-Benzoyl-4-(4-fluorophenylsulphonamido)1,2,2a,3,4,5-hexahydrobenz[c,d]indole

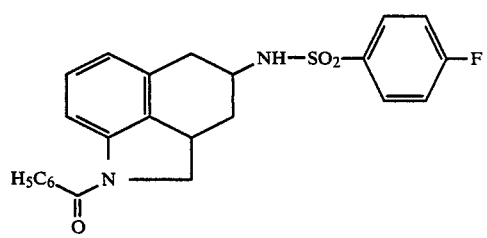

13.1 g of 1-benzoyl-4-amino-1,2,2a,3,4,5-hexahydrobenz[c,d]indole together with 6.06 g of triethylamine are dissolved in 700 ml of dichloromethane. 10 g of 4-fluorobenzenesulphonyl chloride in 100 ml of dichloromethane are added dropwise to this mixture at room temperature. The mixture is stirred for a further hour at room temperature. It is then washed twice using 2N sulphuric acid, once using water, twice using 2N sodium hydroxide solution and once using water. After drying using sodium sulphate and evaporation, a residue is obtained which gives 15.3 g of crystalline product from an ethyl acetate/ether mixture.

Yield: 75.1% of theory
m.p.: 172° C.
$R_f$ value: 0.39 (toluene:ethanol 6:1)

Intermediate (C)

4-(4-Fluorophenylsulphonamido)-1,2,2a,3,4,5-hexahydrobenz[c,d]indole

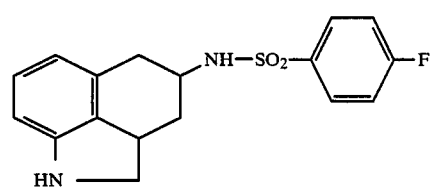

15 g of 1-benzoyl-4-(4-fluorophenylsulphonamido)-1,2,2a,3,4,5-hexahydrobenz[c,d]indole are heated under reflux for 24 h in a mixture of 350 ml of 10% strength potassium hydroxide solution and 370 ml of isopropanol. After cooling, the reaction solution is evaporated in vacuo to half its volume, 1 l of water is added and the mixture is extracted 4 times with ethyl acetate. The combined organic phases are dried using sodium sulphate and evaporated. The solid residue is crystallized from toluene. 9.2 g of crystalline product are thus obtained.

Yield: 80.7% of theory
m.p.: 168° C.
$R_f$ value: 0.27 (toluene:ethyl acetate 8:2)

Intermediate (D)

1-(2-Cyanoethyl)-4-(4-fluorophenylsulphonamido)-1,2,2a,3,4,5-hexahydrobenz[c,d]indole

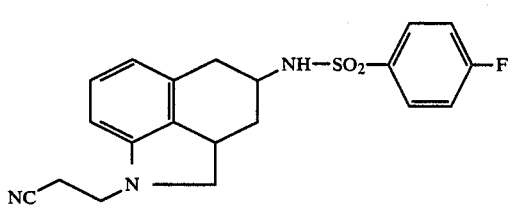

7.9 g of 4-(4-fluorophenylsulphonamido)-1,2,2a,3,4,5-hexahydrobenz[c,d]indole are dissolved in 80 ml of freshly distilled acrylonitrile and 0.7 g of copper(II) acetate are added. The reaction solution is heated for 1 h under reflux. After cooling, it is evaporated in vacuo and the residue is chromatographed on 20 g of silica gel 60 using toluene-ethyl acetate in the ratio 10:1 to 6:1 as the eluant. A fraction is thus obtained which, after evaporation, gives 7 g of product as an oily residue.

Yield: 76.4% of theory

R$_f$ value: 0.5 (toluene:ethanol 6:1)

EXAMPLE 2

1-(2-Carboxyethyl)-4-(4-fluorophenylsulphonamido)-1,2,2a,3,4,5-hexahydrobenz[c,d]indole

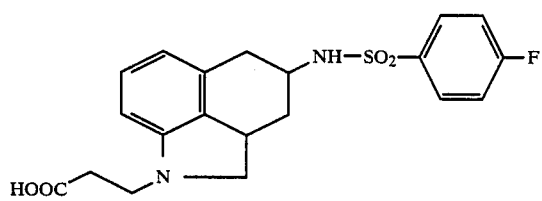

3.5 g of 1-(2-cyanoethyl)-4-(4-fluorophenylsulphonamido)-1,2,2a,3,4,5-hexahydrobenz[c,d]indole are heated for 4 h under reflux in a mixture of 70 ml of isopropanol with 100 ml of 10% strength potassium hydroxide solution. The reaction solution is concentrated in vacuo, diluted with 100 ml of water and extracted twice using ethyl acetate. The aqueous phase is rendered acidic using 6N hydrochloric acid and extracted 3 times with ethyl acetate. The combined organic phases are dried using sodium sulphate and evaporated. The residue gives 2.2 g of crystalline product after recrystallization from isopropanol.

Yield: 60% of theory m.p.: 137° C.

R$_f$ value: 0.57 (toluene:ethanol 3:1)

EXAMPLE 3

1-(2-Cyanoethyl)-4-(4-fluorophenylsulphonamido)-1,3,4,5-tetrahydrobenz[c,d]indole

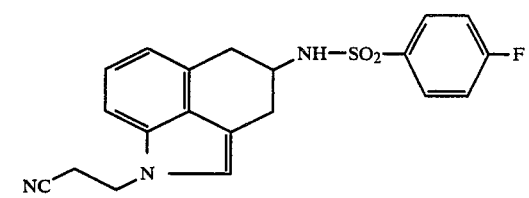

3.5 g of 1-(2-cyanoethyl)-4-(4-fluorophenylsulphonamido)-1,2,2a,3,4,5-hexahydrobenz[c,d]indole together with 3 g of chloranil are heated for 24 h under reflux. After cooling, the reaction mixture is washed 3 times using 1N sodium hydroxide solution, dried using sodium sulphate and evaporated. The residue is chromatographed on 30 g of silica gel 60 using toluene-ethyl acetate in the ratio 10:1 as the eluant. A fraction is thus obtained which, after evaporation, gives 1.43 g of oily product.

Yield: 40% of theory

R$_f$ value: 0.44 (toluene:acetone 3:1)

EXAMPLE 4

1-(2-Carboxyethyl)-4-(4-fluorophenylsulphonamido)-1,3,4,5-tetrahydrobenz[c,d]indole

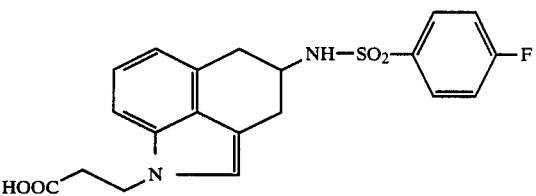

1.4 g of 1-(2-cyanoethyl)-4-(4-fluorophenylsulphonamido)-1,3,4,5-tetrahydrobenz[c,d]indole are heated for 4 h under reflux in a mixture of 30 ml of isopropanol and 40 ml of 10% strength potassium hydroxide solution. The reaction solution is concentrated in vacuo, diluted with 100 ml of water and extracted twice using ethyl acetate. The aqueous phase is acidified using 6N hydrochloric acid and extracted 3 times using ethyl acetate. After drying using sodium sulphate and evaporating, the residue, for conversion into its sodium salt, is dissolved in 20 ml of methanol, 3,1 ml of 1N NaOH is added and the mixture is evaporated to dryness in vacuo. 1.3 g of solid sodium salt are thus obtained.

Yield: 84% of theory

R$_f$ value: 0.27 (toluene:ethanol 6:1)

EXAMPLE 5 (USE EXAMPLE)

For determination of the thrombocyte aggregation-inhibiting action, blood from healthy subjects of both sexes was used. One part of 3.8% strength aqueous sodium citrate solution was added to 9 parts of blood as anticoagulant. Platelet-rich citrate plasma (PRP) was obtained from this blood by means of centrifugation (Jürgens/Beller, Klinische Methoden der Blutgerinnungsanalyse (Clinical Methods of Blood Coagulation Analysis); Thieme Verlag, Stuttgart, 1959).

For these investigations, 0.8 ml of PRP and 0.1 ml of the active compound solution were preincubated at 37° C. in the waterbath. The thrombocyte aggregation was then determined by the turbidimetric method (Borth, B. V. R., J. Physiol. (London), 162, 67, 1962) in an aggregometer at 37° C. (Therapeutisische Berichte 47, 80–86, 1975). To do this, 0.1 ml of collagen, an aggregation-initiating agent, was added to the preincubated sample. The change in optical density in the PRP sample was recorded over a period of 6 minutes and the deflection after 6 minutes was determined. To do this, the percentage inhibition in comparison with the control is calculated.

The range of the minimum effective concentration is given as the limiting concentration (Table 3).

TABLE 3

| Example No. | Inhibition mg/l (limiting concentration) |
|---|---|
| 2 | 0.03–0.1 |

It will be understood that the specification and examples are illustrative but not limitative of the present invention and that other embodiments within the spirit and scope of the invention will suggest themselves to those skilled in the art.

What is claimed is:

1. A polyhydrobenz[c,d]indolesulphonamide of the formula

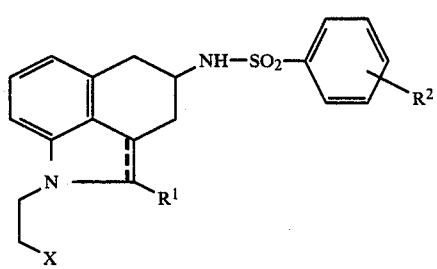
(I)

in which
R$^1$ is hydrogen, C$_{6-12}$ aryl or C$_{1-12}$ alkyl,
R$^2$ is hydrogen, halogen, C$_{1-12}$ alkyl, C$_{1-12}$ alkoxy, trifluoromethyl, trifluoromethoxy, hydroxyl, C$_{7-14}$ aralkoxy or
a group of the formula

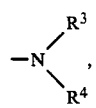

R$^3$ and R$^4$ each independently is hydrogen, C$_{1-12}$ alkyl, C$_{6-12}$ aryl, C$_{7-14}$ aralkyl, benzoyl or C$_{1-6}$ alkylcarbonyl and
X is cyano or carboxyl, or a physiologically acceptable salt thereof.

2. A polyhydrobenz[c,d]indolesulphonamide or salt according to claim 1, in which
R$^1$ is hydrogen, phenyl or lower alkyl,
R$^2$ is hydrogen, fluorine, chlorine, bromine, lower alkyl, lower alkoxy, trifluoromethyl, hydroxyl, benzyloxy or
a group of the formula

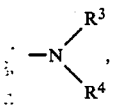

and R$^3$ and R$^4$ each independently is hydrogen, lower alkyl, phenyl, benzyl or acetyl.

3. A polyhydrobenz[c,d]indolesulphonamide or salt according to claim 1, in which
R$^1$ is hydrogen, methyl, ethyl, propyl or isopropyl,
R$^2$ is hydrogen, fluorine, chlorine, methyl, ethyl, propyl, isopropyl, methoxy, ethoxy, propoxy, isopropoxy, trifluoromethyl or a group of the formula

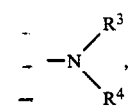

and
R$^3$ and R$^4$ each independently is hydrogen, methyl, ethyl or propyl.

4. A polyhydrobenz[c,d]indolesulphonamide according to claim 1 of the formula

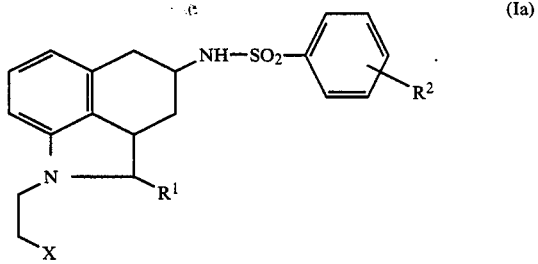
(Ia)

5. A polyhydrobenz[c,d]indolesulphonamide according to claim 1 of the formula

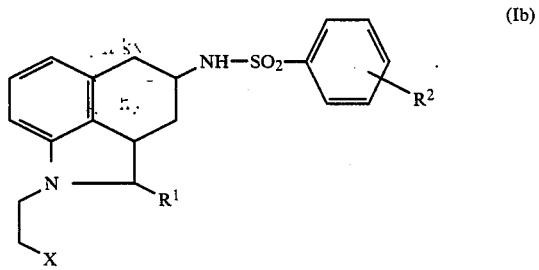
(Ib)

6. A compound according to claim 1, wherein such compound is 1-(2-cyanoethyl)-4-(4-fluorophenylsulphonamido)-1,2,2a,3,4,5-hexahydrobenz[c,d]indole of the formula

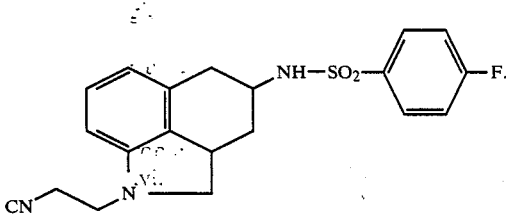

7. A compound according to claim 1, wherein such compound is 1-(2-carboxyethyl)-4-(4-fluorophenylsulphonamido)-1,2,2a,3,4,5-hexahydrobenz[c,d]indole of the formula

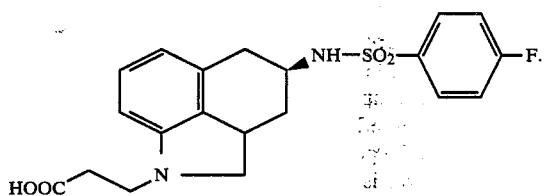

8. A compound according to claim 1, wherein such compound is 1-(2-cyanoethyl)-4-(4-fluorophenylsulphonamido)-1,3,4,5-tetrahydrobenz[c,d]indole of the formula

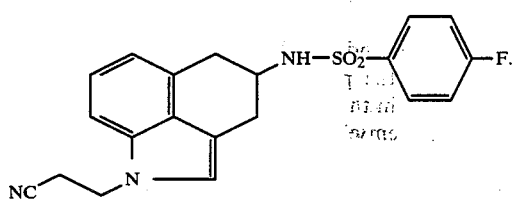

9. A compound according to claim 1, wherein such compound is 1-(2-carboxyethyl)-4-(4-fluorophenylsulphonamido)-1,3,4,5-tetrahydrobenz[c,d]indole of the formula

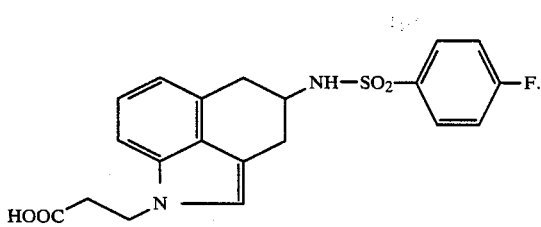

10. A thrombocyte aggregation-inhibiting composition comprising an amount effective therefor of a compound according to claim 1 and a pharmaceutically acceptable diluent.

11. A unit dose of a composition according to claim 10 in the form of a tablet, capsule or ampoule.

12. A method of inhibiting aggregation of thrombocytes in a patient in need thereof which comprises administering to such patient an amount effective therefor of a compound according to claim 1.

13. The method according to claim 12, wherein such compound is
1-(2-cyanoethyl)-4-(4-fluorophenylsulphonamido)-1,2,2a,3,4,5-hexahydrobenz[c,d]indole,
1-(2-carboxyethyl)-4-(4-fluorophenylsulphonamido)-1,2,2a,3,4,5-hexahydrobenz[c,d]indole,
1-(2-cyanoethyl)-4-(4-fluorophenylsulphonamido)-1,3,4,5-tetrahydrobenz[c,d]indole, or
1-(2-carboxyethyl)-4-(4-fluorophenylsulphonamido)-1,3,4,5-tetrahydrobenz[c,d]indole.

14. A hexahydrobenzindolesulphonamide of the formula

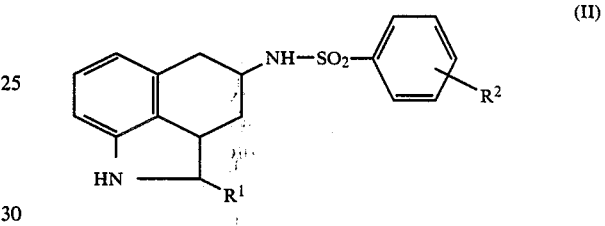

(II)

in which
$R^1$ is hydrogen, $C_{6-12}$ aryl or $C_{1-12}$ alkyl,
$R^2$ is hydrogen, halogen, $C_{1-12}$ alkyl, $C_{1-12}$ alkoxy, trifluoromethyl, trifluoromethoxy, hydroxyl, $C_{7-14}$ aralkoxy or
a group of the formula

and $R^3$ and $R^4$ each independently is hydrogen, $C_{1-12}$ alkyl, $C_{6-12}$ aryl, $C_{7-14}$ aralkyl, benzoyl or $C_{1-6}$ alkylcarbonyl.

* * * * *